United States Patent [19]

Balaban et al.

[11] 4,281,122

[45] Jul. 28, 1981

[54] PREPARATION OF SODIUM DICHLORO-S-TRIAZINE TRIONE COMPOSITIONS

[75] Inventors: Stephen M. Balaban, Chesterfield, Mo.; Raymond C. Cox, Belleville, Ill.

[73] Assignee: Monsanto Company, St. Louis, Mo.

[21] Appl. No.: 149,213

[22] Filed: May 12, 1980

[51] Int. Cl.³ .......................................... C07D 251/36
[52] U.S. Cl. ..................................................... 544/190
[58] Field of Search ......................................... 544/190

[56] References Cited

U.S. PATENT DOCUMENTS

| | | | |
|---|---|---|---|
| 3,178,429 | 4/1965 | Vazopolos | 260/248 |
| 3,294,797 | 12/1966 | Shallenberger et al. | 260/248 |
| 3,336,228 | 8/1967 | Fuchs et al. | 252/99 |
| 3,397,206 | 8/1968 | Nicolaisen | 544/190 |
| 4,122,267 | 10/1978 | Nelson et al. | 544/190 |

*Primary Examiner*—John M. Ford
*Attorney, Agent, or Firm*—George R. Beck

[57] ABSTRACT

Sodium dichloro s-triazine trione compositions can be prepared in high yields with essentially no waste disposal requirements, without need for refrigeration, with ease of process control and surprisingly low generation of hazardous byproduct nitrogen trichloride by chlorinating a sodium s-triazine trione in an aqueous mixture wherein the triazine compounds are essentially completely in the liquid phase and the amount of water is below about 65%.

12 Claims, No Drawings

PREPARATION OF SODIUM DICHLORO-S-TRIAZINE TRIONE COMPOSITIONS

BACKGROUND OF THE INVENTION

Sodium dichloro s-triazine trione (herein at times called "SDT") has been heretofore manufactured by chlorinating disodium cyanurate and then reacting the resulting dichlorocyanuric acid with sodium hydroxide, e.g. as described in U.S. Pat. No. 3,294,797 issued Dec. 27, 1966 to C. D. Shallenberger et al. However, that preparation of SDT has the disadvantage of producing an aqueous sodium chloride waste stream of substantial size from the disodium cyanurate chlorination step.

It has also been known that salts of dichlorocyanuric acid can be prepared by chlorinating cyanuric acid in the presence of the hydroxide of the desired metal, e.g. as described in U.S. Pat. No. 3,336,228 issued Aug. 15, 1967 to R. J. Fuchs et al.

More recently, it has been found that useful compositions containing SDT and byproduct sodium chloride can be prepared in high yields with essentially no waste disposal requirements by chlorinating a sodium s-triazine trione in an aqueous slurry and then converting the slurry to a solid composition by water removal (e.g. spray drying) as described in U.S. Pat. No. 4,122,267 issued Oct. 24, 1978 to G. D. Nelson et al. Although the discovery was a significant advance in the art, difficulties have been experienced at times in handling the reaction slurry, e.g. line plugging and undesirably long reaction times. In addition, because the chlorination is exothermic, a refrigeration system is generally required to maintain the reaction temperature of 10°-60° C. (preferably 40°-45° C.) prescribed in that patent. It would be less costly to carry out the reaction without such refrigeration, but it has been expected that a higher reaction temperature would result in formation of substantial quantities of nitrogen trichloride, a byproduct which is toxic and highly explosive. See U.S. Pat. No. 3,178,429 issued Apr. 13, 1965 to S. Vazopolos.

An improved process by which such SDT compositions can be prepared in high yields with essentially no waste disposal requirements is very desirable, and it is an object of this invention to provide such a process. Another object is such a process which does not require use of a refrigeration system. Another object is such a process in which the reaction mixture is subject to more convenient handling and control. A further object is such a process having a relatively short reaction time. An important object is such a process which does not result in formation of $NCl_3$ in amounts too large for non-hazardous disposal. Still another object is to provide SDT-containing compositions prepared in accordance with such a process. These and other objects of the invention will be more fully apparent from the following detailed disclosure, in which all parts and percentages are by weight and all temperatures are in degrees Centigrade except where otherwise noted.

SUMMARY OF THE INVENTION

In accordance with this invention, the above objects are achieved by an improved process for preparing a sodium dichloro s-triazine trione composition by chlorinating a sodium s-triazine trione in an aqueous mixture having a liquid phase, said process being improved by maintaining the triazine compounds in the mixture essentially completely dissolved in the liquid phase and the amount of water in the mixture below about 65%. In preferred embodiments, the triazine compounds in the mixture are maintained essentially completely dissolved in the liquid phase by maintaining the temperature of the mixture between about 65° and about 80°, within which range it has been found that surprisingly small amounts of $NCl_3$ are formed. Also provided by the invention are the SDT-containing compositions prepared in accordance with that process improvement.

DETAILED DESCRIPTION OF THE INVENTION

The process of this invention can be carried out generally in accordance with the teaching of U.S. Pat. No. 4,122,267, the disclosure of which is incorporated herein by reference. However, as aforesaid, the present process is improved by maintaining the triazine compounds in the chlorination reaction mixture essentially completely dissolved in the liquid phase of that mixture, rather than substantially in the solid phase as they are in the reaction slurry prescribed in that patent. Thus the present process can be carried out using the alternate prechlorination procedures described in U.S. Pat. No. 4,122,267, i.e., s-triazine trione and an alkaline sodium compound (e.g. sodium hydroxide) can be separately fed to the chlorination reaction mixture or, generally more desirably, the s-triazine trione and sodium compound can be prereacted outside the chlorination reaction mixture to form a sodium s-triazine trione which is then fed to such a reaction mixture for chlorination. The former mode of operation is generally somewhat more complicated to control, but can be carried out satifactorily by maintaining proper relative feed rates of the reactants to the chlorination reaction mixture in response to continuous monitoring of the pH and reduction-oxidation potential of the resulting reaction mixture.

Also as aforesaid, the amount of water in the reaction mixture of this invention should be maintained below about 65%. Although the solubility of unchlorinated sodium s-triazine triones in water is normally quite low, it has been found that the triazine compounds in the aqueous reaction mixture of this invention can be maintained essentially completely dissolved in the liquid phase of that mixture, even when the mixture contains less than 65% water, by maintaining the temperature of the mixture between about 65° and about 80°, preferably between about 72° and about 78°. Since the reaction mixture of the present process is thus at a higher temperature than that described in U.S. Pat. No. 4,122,267, it is normally subsequently cooled, typically to between about 20° and about 35° and preferably between about 25° and about 30°, to substantially solidify the triazine compounds in the mixture, leaving a slurry which may be thereafter satisfactorily converted to an essentially completely solid composition by water removal in accordance with various well known techniques, e.g. tray drying, rotary drying, vacuum rotary drying, drum drying or, preferably, spray drying. These and other useful water removal techniques are described in the Encyclopedia of Chemical Technology edited by Kirk and Othmer, Interscience Encyclopedia, Inc., New York, N.Y., Vol. 5, pp. 232-65 (1950).

One advantage of maintaining the proportion of water in the reaction mixture of the present process below about 65% is that, after being cooled to substantially solidify the triazine compounds as described hereinbefore, the mixture contains little enough water that it can be converted to an essentially completely solid composition by conventional drying techniques without need for filtration which would produce a liquid aqueous waste stream of NaCl and small amounts of SDT posing waste disposal problems. Rather, as in U.S. Pat. No. 4,122,267, removal of the water in a drying step leaves a stream of relatively pure water vapor which in many instances can be recycled back to the process. In preferred embodiments, the reaction mixture of this process contains less than about 60% water. Normally it contains at least about 40% and, even more usually, at least about 50% water. As expressed in this specification and the appended claims, the amount of water in the reaction mixture does not include the water of hydration of hydrated compounds, if any, in the reaction mixture.

The amount of water in the present reaction mixture is generally controlled most conveniently by regulating the amounts of water used in feeding the s-triazine trione and sodium compound to that mixture. Thus, whether or not the s-triazine trione and sodium compound are prereacted to form a sodium s-triazine trione outside the chlorination reactor, it is advantageous to begin with an aqueous slurry containing from about 25% to about 35% s-triazine trione, and an aqueous solution containing reactive sodium in a concentration, calculated as NaOH, of at least about 30%, preferably at least about 35%, and even more desirably at least about 40%, up to about 50% or higher.

The sodium s-triazine trione used in the process of this invention can be monosodium s-triazine trione, more desirably disodium s-triazine trione or a mixture thereof with trisodium s-triazine trione or, generally most advantageously, essentially all trisodium s-triazine trione. As fed to the reaction mixture used in this invention, such sodium s-triazine triones are normally, but not necessarily, essentially unchlorinated. The degree of chlorination, if any, of such sodium s-triazine triones is of course less than that of the desired SDT product.

As used in this specification and the appended claims, the term "triazine compounds" includes unsubstituted s-triazine trione, the aforementioned sodium s-triazine triones, the SDT prepared in accordance with this invention, and any other compounds containing a triazine ring. In the present process, the reaction mixture can contain any proportions of sodium and such triazine compounds which are conductive to production of SDT therein. Preferably the sodium reacted with or available for reaction with the triazine compounds in the reaction mixture is present in an amount between about 2.5 and about 3.1, preferably at least about 3.02 atoms of sodium per mole of triazine ring, i.e., per mole of each compound containing at least one triazine ring multiplied by the number of triazine rings in that compound. These proportions are applicable whether unsubstituted s-triazine trione and reactive sodium (e.g. as NaOH) are separately fed to the chlorination reaction mixture or if they are prereacted to form a sodium s-triazine trione for subsequent use in the process of this invention.

In the present process, superior results are obtained when the concentration of sodium in the reaction mixture is relatively high, i.e., generally at least about 12% and preferably at least about 15% up to about 20% or even higher, calculated as NaOH. The chlorine can be fed to the reaction mixture in any form which provides sufficient readily available chlorine for preparation of the SDT, e.g. an alkali metal hypochlorite, but normally most desirably as chemically uncombined chlorine, which may be conveniently bubbled through the mixture in a proportion suitable to provide the desired SDT product. Proportions of the chlorine and sodium compound in the reaction mixture are most desirably controlled to maintain the pH of the reaction mixture between about 5 and about 7.5, preferably at least about 5.5, preferably not above about 7 and even more desirably not above about 6.5, although somewhat higher or lower pH may be satisfactory in some instances.

Using the improved process described herein, problems normally associated with slurry handling (e.g. line plugging, difficulties in uniform mixing, etc.) are eliminated in the reaction vessel and its effluent lines. Further, the aforementioned liquid-phase reaction temperatures permit cooling of the reaction mixture to be carried out with water from a conventional cooling tower, rather than the more expensive refrigerated brine system typically needed to maintain the reaction temperature at the lower levels prescribed in U.S. Pat. No. 4,122,267. Moreover, the present process typically provides a high yield of SDT (from at least about 85% up to about 95% or higher, based on the moles of sodium s-triazine trione available for chlorination in the reaction mixture) within a reaction time which is relatively short, i.e., generally less than about 30 minutes and most usually between about 5 and about 20 minutes of average residence time in the reaction mixture. Thus, on the basis of the theoretical yield of SDT, about 5% is lost through ring decomposition with a ten-minute average reaction time, and about 12% is lost after 30 minutes of residence time. As in the process of U.S. Pat. No. 4,122,267, the present invention also provides useful compositions containing such SDT with essentially no waste disposal requirements, in that byproduct NaCl is conveniently retained in the solid compositions prepared by drying of the cooled reaction mixture, without detriment to performance of the SDT in conventional bleaching and sanitizing uses.

In addition, the present process generates far less $NCl_3$ than expected and, in fact, so little that an air or inert gas purge of the reactor at a very low rate is sufficient to reduce the concentration of $NCl_3$ to a negligible value. Although it has been theorized by Becanne et al in "Fisons TCC Process", *Chemical Processing*, pp. 515–19 (Oct. 1967) that $NCl_3$ may decompose to $N_2$ and $Cl_2$ at the higher of certain unspecified temperatures used in pneumatic flash drying of damp trichloroisocyanuric acid, it is very surprising that $NCl_3$ is formed in only very small amounts under the chlorination conditions used in the process of this invention.

Following is a specific example of the process of this invention. This example is illustrative only and does not imply any limitations on the scope of the invention.

EXAMPLE

In a steady-state, continuous process, 68.2 parts of a 50% solution of NaOH in water, 36.4 parts of 98% pure unsubstituted s-triazine trione having an average particle size of 100 microns and 99.5 parts of water are metered into a tank containing a well-agitated, aqueous slurry of trisodium s-triazine trione. The average residence time of the slurry in that tank is less than 10 minutes to minimize biuret formation. A small side stream is taken off, filtered and the supernatant titrated continuously to provide a control point for a trim pump which adds enough NaOH to achieve a 3.05:1 ratio of sodium atoms to moles of triazine ring in the tank.

The slurry is fed from that tank to a glass-lined reactor in which it is chlorinated with 40.5 parts of gaseous $Cl_2$ in a liquid reaction mixture having a temperature maintained within the range of 75°±3° C. by tower cooling water in coils inside the reactor, and a pH maintained between 5.5 and 7.5. Under those conditions, the reaction mixture contains essentially no solid phase and, on the average, 56.5% water. In the reaction mixture, the NaOH concentration is 20% and the average residence time of the triazine compounds is 10 minutes.

The gas space in the reactor is purged with air which exits upwardly to a scrubber in which it is scrubbed with 875 parts of liquid reaction mixture circulated from the reactor downwardly through the scrubber. Another 241.9 parts of reaction product containing 58 parts SDT, 35 parts NaCl and 148.9 parts $H_2O$ flow from the reactor to a double pipe or spiral heat exchanger in which it is cooled is 25° C., converting it to a slurry which is then fed to a conventional spray dryer. 2.7 parts leave the system as decomposition gases. A centrifugal turbine disperses the slurry in the spray drying chamber having 220° C. inlet and 85° C. outlet air temperatures, producing a solid product containing 59% SDT, 36% NaCl and 5% moisture.

Under these conditions, only 0.003 parts of $NCl_3$ are produced in the reaction mixture. In a reactor containing a 1,600 kg liquid charge, this rate of $NCl_3$ generation requires an air purge of only 10 SCFM to reduce the $NCl_3$ concentration in the reactor to a negligible value. The yield of sodium dichloro s-triazine trione is 95%, using a ten-minute average residence time, and chlorine utilization is 96%.

We claim:

1. In a process for preparing a sodium dichloro s-triazine trione composition by chlorinating a sodium s-triazine trione in an aqueous mixture having a liquid phase, the improvement which comprises maintaining the triazine compounds in said mixture essentially completely dissolved in said liquid phase and the amount of water in said mixture below about 65% by weight.

2. The process improvement of claim 1 wherein said compounds are maintained essentially completely dissolved in said liquid phase by maintaining the temperature of said mixture between about 65° and about 80° C.

3. The process improvement of claim 1, said mixture containing between about 2.5 and about 3.1 atoms of sodium per mole of triazine ring in said mixture.

4. The process improvement of claim 1, said mixture having a pH between about 5 and about 7.5.

5. The process improvement of claim 1, said mixture containing at least about 40% water by weight.

6. The process improvement of claim 1 wherein the sodium s-triazine trione has been prepared outside said mixture.

7. The process improvement of claim 1, said mixture consisting essentially of triazine compounds, sodium hydroxide, sodium chloride, chlorine and water.

8. The process improvement of claim 7 wherein said compounds are maintained essentially completely dissolved in said liquid phase by maintaining the temperature of said mixture between about 72° and about 78° C.

9. The process improvement of claim 7, said mixture containing between about 3.02 and about 3.1 atoms of sodium per mole of triazine ring in said mixture.

10. The process improvement of claim 1 wherein at least about 85 mole percent of the sodium s-triazine trione in the mixture is reacted to form sodium dichloro s-triazine trione.

11. The process improvement of claim 10 which further comprises cooling the resulting mixture to substantially solidify the triazine compounds in said mixture, and then converting the resulting slurry to an essentially completely solid composition by removing water from said slurry.

12. The process improvement of claim 11 wherein the removing of water is carried out by spray drying said slurry.

* * * * *